US006874634B2

(12) United States Patent
Riley

(10) Patent No.: US 6,874,634 B2
(45) Date of Patent: Apr. 5, 2005

(54) VARIABLY STACKABLE STERILIZATION TRAY SYSTEM

(75) Inventor: Edward D. Riley, Falmouth, ME (US)

(73) Assignee: Riley Medical, Inc., Auburn, ME (US)

( * ) Notice: Subject to any disclaimer, the term of this patent is extended or adjusted under 35 U.S.C. 154(b) by 97 days.

(21) Appl. No.: 10/406,304

(22) Filed: Apr. 3, 2003

(65) Prior Publication Data

US 2004/0144670 A1 Jul. 29, 2004

Related U.S. Application Data

(60) Provisional application No. 60/443,440, filed on Jan. 29, 2003.

(51) Int. Cl.[7] .............................................. A61L 2/20
(52) U.S. Cl. ....................... 206/439; 206/370; 206/509; 422/310
(58) Field of Search ................................ 206/363, 364, 206/370, 438, 439, 509, 511; 422/300, 310

(56) References Cited

U.S. PATENT DOCUMENTS

| 4,643,303 A | * | 2/1987 | Arp et al. .................... 206/370 |
| 4,798,292 A | * | 1/1989 | Hauze ......................... 206/439 |
| 5,424,048 A | * | 6/1995 | Riley .......................... 422/300 |
| 5,524,755 A | * | 6/1996 | Deeds ......................... 206/370 |
| 5,540,901 A | * | 7/1996 | Riley .......................... 422/300 |
| 5,573,741 A | * | 11/1996 | Riley .......................... 422/300 |
| 5,699,925 A | * | 12/1997 | Petruzzi ...................... 220/4.27 |
| 5,950,828 A | * | 9/1999 | Bal ............................ 206/370 |
| 6,116,452 A | * | 9/2000 | Hamel et al. ................. 220/318 |
| 6,371,320 B2 | * | 4/2002 | Sagol ......................... 220/4.27 |
| 6,585,942 B1 | * | 7/2003 | Bussell et al. ............... 422/300 |
| 6,713,029 B1 | * | 3/2004 | Krafft et al. ................. 422/300 |

\* cited by examiner

Primary Examiner—John A. Ricci
(74) Attorney, Agent, or Firm—Cesari and McKenna, LLP; John F. McKenna

(57) ABSTRACT

A tray system composed of a vertical stack of trays especially adapted to contain, and protect surgical instruments being carried from a sterilizer to an operating site. The trays may have various heights and be arranged in any order in the stack. Each tray includes a plurality of latches, each latch having an arm swingably mounted to the tray and terminated by a projection spaced a selected distance $D_1$ above the tray rim or top when the latch is swung to its latching position. Each tray also includes a corresponding plurality of latching surfaces located under the latches on that tray. The distance $D_2$ between the seating surfaces and latching surfaces of each tray corresponds substantially to the distance $D_1$ of that tray. This enables the latch arms of each tray to be latched to the latching surfaces of an overlying tray in the stack or to a cover so as to form a closed compact transportable package. Different latch embodiments for securing the trays together are also disclosed.

17 Claims, 4 Drawing Sheets

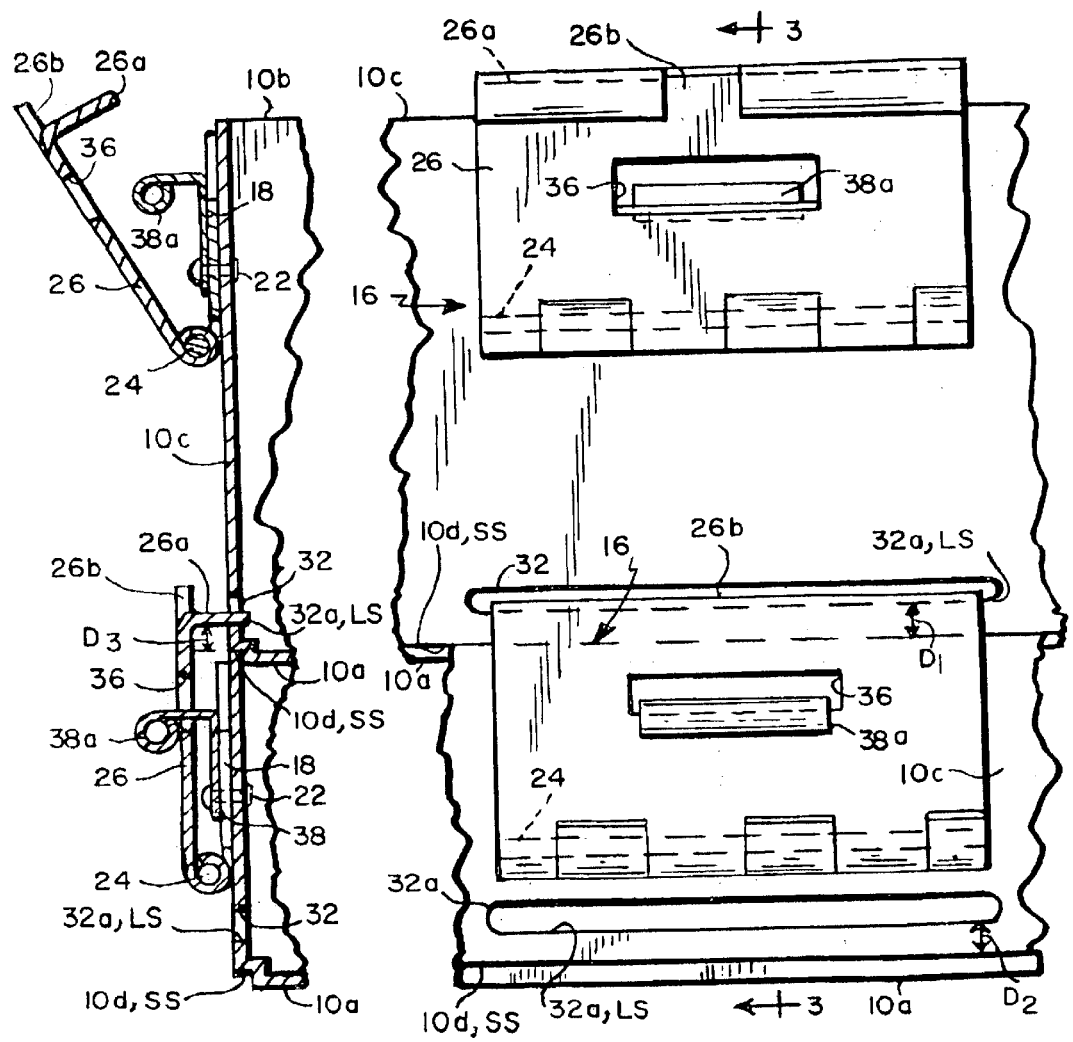

ent No. 60/443,440, filed Jan. 29, 2003.

VARIABLY STACKABLE STERILIZATION TRAY SYSTEM

CROSS-REFERENCE TO RELATED APPLICATIONS

This application claims the benefit of Provisional Application No. 60/443,440, filed Jan. 29, 2003.

BACKGROUND OF THE INVENTION

1. Field of the Invention

This invention relates to a variably stackable tray system. It relates more particularly to a tray system or package for use in connection with sterilizing, delivering and presenting surgical instruments and materials in an aseptic condition prior to surgery and preventing contamination from those instruments following surgery.

It is normal procedure to provide appropriate types and quantities of surgical instruments and materials for a specific surgical procedure as a unitary package that has been sterilized previously. Prior to or during an operation, the instruments and materials are removed from the package and laid out on a Mayo table or other surface so that they are readily accessible to the surgeon performing the operation.

2. Description of the Prior Art

Conventionally, an instrument package includes an outer container for enclosing trays arranged in layers or in a stack within the container. The open top of the container is invariably closed by a cover or lid which may be latched to the container so that the container contents are protected and maintained in a sterile condition when a package is transported from the sterilizer to the operating area.

Preferably, the instrument package for a particular procedure has the various instruments and materials laid out on the trays in the order in which they will be used for that procedure. In other words, the group of instruments that will be used first will be in the uppermost tray in the container. When those instruments have been used or are no longer required, that uppermost tray is removed exposing the group of instruments presented on the underlying tray. When that second group of instruments is no longer required, that second tray is removed exposing the instruments in the next tray, and so on down to the lowermost tray in the container. When the surgical procedure is completed, the instruments and trays may be returned to the container and the container closed so that the entire package can be carried to a cleaning area without risk of contamination from the instruments therein. U.S. Pat. No. 5,540,901 shows a sterilization tray system or package of this general type.

While the sterilization tray system just described is quite satisfactory in many respects and may be used in many surgical procedures, it does not take into account that some procedures may require the use of more instruments and materials than others. In other words, for a complicated surgical procedure, the outer container must be able to accommodate several instrument trays stacked within the container, while a simple surgical procedure may only require one or two instrument trays within the outer container. This means that an outer container capable of accommodating the number of trays required by the most complicated procedure must be used even though a lesser number of instruments may suffice for most operations. Clearly, then, the overall cost and the size of many, if not most, instrument packages are larger than they need be. Also, the height of the outer container limits the maximum number of trays that can be accommodated by the container so that the usual tray system cannot be used for that rare surgical procedure that may require an unusually large number of instruments and/or materials.

SUMMARY OF THE INVENTION

Accordingly, it is an object of the present invention to provide a sterilization tray system which can be composed of any number of instrument trays arranged in layers.

A further object of the invention is to provide a system of this type composed of layers of instrument trays having various heights.

Yet another object of the invention is to provide such a tray system composed of a plurality of trays of which may have various different heights and which can be stacked in any order and secured together to form a single secure compact transportable package.

A further object of the invention is to provide a unitary tray system composed of a plurality of trays which may be releasably secured together in layers with a cover or lid closing the top of the uppermost tray.

Another object of the invention is to provide a tray system or package composed of a plurality of instrument trays each adapted to be arranged in a stack and including special latch assemblies which may releasably connect to an overlying tray in the stack as well as to a lid covering the open top of the tray.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, the tray system comprises a plurality of open top trays having substantially identical length and width dimensions but whose heights may vary. The trays have seating surfaces at their undersides and can be nested together to form layers of a stack so that the open top of each tray is closed by the overlying tray. Preferably, the system also includes a cover or lid for closing the open top of the uppermost tray in the stack.

In accordance with the invention, each tray is provided with a plurality of latches. Each tray latch is pivotally connected to a perimeter wall of the tray and includes a lip or flange spaced opposite the latch pivot. The latch may be swung between a latching position wherein the lip or flange overhangs the rim of the tray and engages a latching surface of an adjacent tray or cover in the stack and an unlatching position wherein the lip or flange is spaced laterally from that rim. Preferably, each latch also includes means for releasably locking the latch in its latching position.

It is a feature of the invention that when the latches on each tray are in the latching position, the lips or flanges of the latches are spaced above the rim of that tray a distance substantially corresponding to the distance between the seating and latching surfaces of the tray. This allows trays of various heights to be stacked in any order and latched together to form a single, easily transportable package which may also include a cover latched to the uppermost tray in the stack.

Thus, the present tray system or package composed of a stack of different height trays can accommodate various groups of instruments having various sizes such that the instruments can be arranged in the package in the order of use for a particular surgical procedure. Therefore, the number and height of the trays in a particular package or system can be customized to the set of instruments required for a particular surgical procedure thereby minimizing the size and cost of the instrument package required for that procedure. Furthermore, the present system is devoid of the outer container required by prior tray systems of this general type, resulting in additional cost savings.

BRIEF DESCRIPTION OF THE DRAWINGS

For a fuller understanding of the nature and objects of the invention, reference should be made to the following detailed description taken in connection with the accompanying drawings, in which:

FIG. 2 is an end view on a larger scale showing the lower two trays of the FIG. 1 system;

FIG. 3 is a sectional view taken along line 3—3 of FIG. 2;

DETAILED DESCRIPTION OF ILLUSTRATIVE EMBODIMENTS

Figure 1:
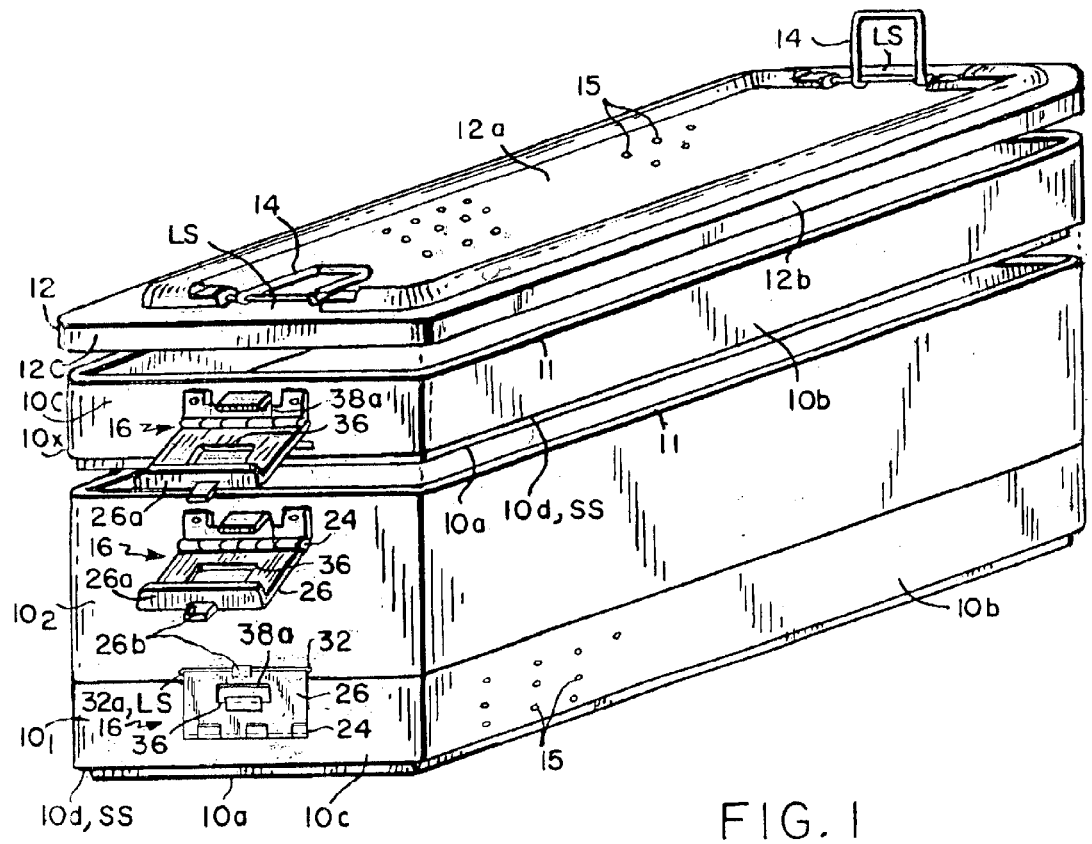
FIG. 1 is an exploded isometric view of a tray system incorporating the invention.

Referring to FIG. 1 of the drawings, the present tray system comprises a plurality of similarly shaped trays $10_1$, $10_2$ ... $10_X$ which may be nested or seated one atop the other to form a vertical stack. In the illustrated system, the trays are of a sterilizable plastic material, are generally rectangular and are used to house medical instruments or materials. However, they could just as well be made of metal and have other cross-sectional shapes such as circular, triangular, elliptical, etc., and they could be used to contain other articles. The illustrated trays have a length of about 8 inches, a width of about 9 inches, but their heights may vary. For example, trays $10_1$ and $10_X$ may have a height of about 2 inches, while the tray $10_2$ may have a height of about 4 inches. As we shall see, a given package or system may consist of any number of trays having various heights arranged in any order in the stack.

Each illustrated tray has a bottom wall 10a, a perimeter wall extending up from the bottom wall consisting of segments in the form of a pair of opposite side walls 10b, 10b, and a pair of opposite end walls 10c, 10c. The tray has an open top encircled by a rim 11 at the top of the perimeter wall defining a rim plane. Preferably, the bottom wall 10a of each tray is set in from the perimeter wall segments 10b, 10c of that tray to form an overhang or overhangs 10d that defines a seating surface or surfaces SS around the bottom wall. The seating surface(s) defines a seating plane that is spaced parallel to the rim plane so that when a tray is set on the rim 11 of an underlying tray, the upper tray will nest in the lower tray such that the two trays will be maintained in vertical alignment as shown at $10_1$ and $10_2$ in FIGS. 1 to 3. The seating surface SS could of course be composed of a plurality of separate coplanar surfaces, e.g. at the corners of the tray.

As shown in FIG. 1, the tray system preferably also includes a cover or lid 12 for closing the open top of the uppermost tray $10_X$ in the stack. The cover 12 has a generally rectangular top wall 12a and may have a depending skirt extending around wall 12a composed of a pair of opposite side walls 12b, 12b and a pair of opposite end walls 12c, 12c. The skirt may be continuous as shown or interrupted, say, at the corners. In any event, the side and end walls are adapted to overlap the side and end walls of the uppermost tray $10_X$ when the cover 12 is placed on the rim 11 of that tray. Preferably, wire bails 14 are pivotally mounted to the opposite ends of cover 12 to facilitate removing the cover 12 from tray $10_X$ and also to facilitate carrying the entire tray system when the cover 12 and all of the trays $10_1$ to $10_X$ are latched together to form a single package as will be described. As is known in the art, some or all of the walls of the trays and/or cover 12 may be provided with small holes 15 which enable steam to circulate through the trays when the tray package is placed in a sterilizer.

Referring to FIGS. 1 to 3, each tray $10_1$ to $10_X$ includes a plurality of latches 16 for releasably connecting that tray to an overlying tray in the stack or to cover 12. In the illustrated system, each of the latches 16 is mounted to an end wall 10c of the associated tray. Each latch includes a generally rectangular base 18 connected by fasteners 22, e.g. rivets, screws or the like, to the corresponding end wall 10c of that tray. Connected to the lower edge of base 18 by a hinge 24 is an arm 26 which is swingable between a latching position wherein the arm extends up more or less parallel to end wall 10c and an unlatching position wherein the arm is angled away from end wall 10c. As shown in the drawing figures, the upper edge margin of latch arm 26 is bent perpendicular to the remainder of the arm to form a projection or flange 26a. When the arm 26 is in its latching position, the projection or flange 26a overlies the tray rim 11 and when the arm is in its unlatching position, the projection or flange is spaced laterally away from and below that rim.

Preferably also, the latch arm 26 is formed with a finger-engagable tab 26b adjacent to the flange 26a to facilitate moving the latch arm 26 between its two positions.

As shown in FIGS. 1 to 3, each latch 16 on each stacked tray $10_1$ to $10_X$ is mounted so that when its arm 26 is in the latching position, the projection or flange 26a of that arm can engage a latching surface LS of the tray or lid 12 seated on that tray in the stack. In the case of the trays, the latching surfaces LS are the lower edges 32a of slots 32 formed in the tray end walls 10c directly under the latches 16 mounted to those end walls. In the case of the cover 12, the latching surfaces LS are the upper surfaces of the cover end walls or segments 12c, 12c, but they could just as well be the edges of slots formed in those end walls. In any event, the latching surfaces of each tray and the cover define a latching surface plane that is spaced parallel to the seating surface plane of that tray or cover.

Figure 4:
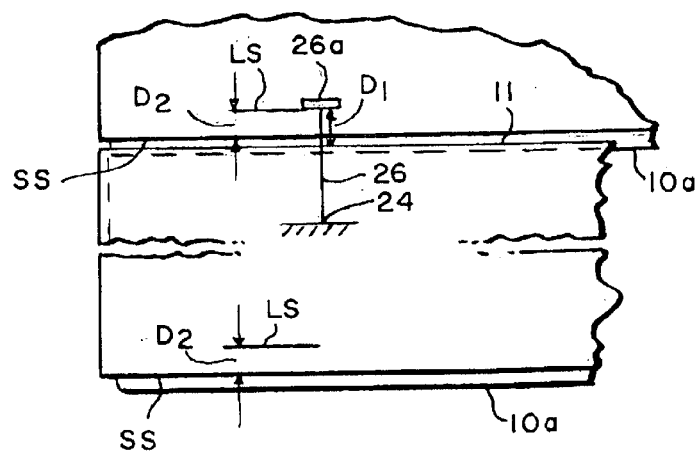
FIG. 4 is a diagrammatic view showing the essential parts of the FIG. 1 system.

Thus, in accordance with the invention and as illustrated diagrammatically in FIG. 4, the latches 16 are situated on their respective trays and their arms 26 are dimensioned such that when each latch arm 26 is in its upright latching position, the underside of the projection or flange 26a of that arm is spaced above the rim 11 of the associated tray a distance $D_1$ which substantially corresponds to the distance $D_2$ between the seating surface SS and the latching surface LS of that tray. That same distance $D_1$ is also more or less equal to the distance between seating surface (the underside of cover wall 12a) and the latching surface LS of cover 12, i.e. the thickness of wall 12a. With this arrangement, the trays $10_1$ to $10_X$ can be nested or seated one atop the other in any order and latched together along with cover 12 to form a single, stable closed package which may be carried about via handles 14 from one place to another.

Preferably, each latch 16 also includes means for releasably locking its latch arm 26 in the latching position. More particularly, each latch arm 26 may be provided with a generally rectangular opening or window 36. Also, a flexible and resilient keeper in the form of a leaf spring 38 may be secured at one end to the base 18 of the latch by the fasteners 22 so that the other, free end of the spring overhangs the opening 36 when arm 26 is in its latching position. The free end of each spring is terminated by a nose 38a which is adapted to project through and engage over the lower edge of opening 36 when the corresponding latch arm 26 is in its vertical latching position as seen by the lower latch 16 in FIGS. 2 and 3. The latch arm 26 may be released from its latching position by lifting up nose 38a thereby disengaging the nose from the edge of the opening 36 and allowing the latch arm to be swung out away from the tray end wall 10c using tab 26b.

Figure 5:
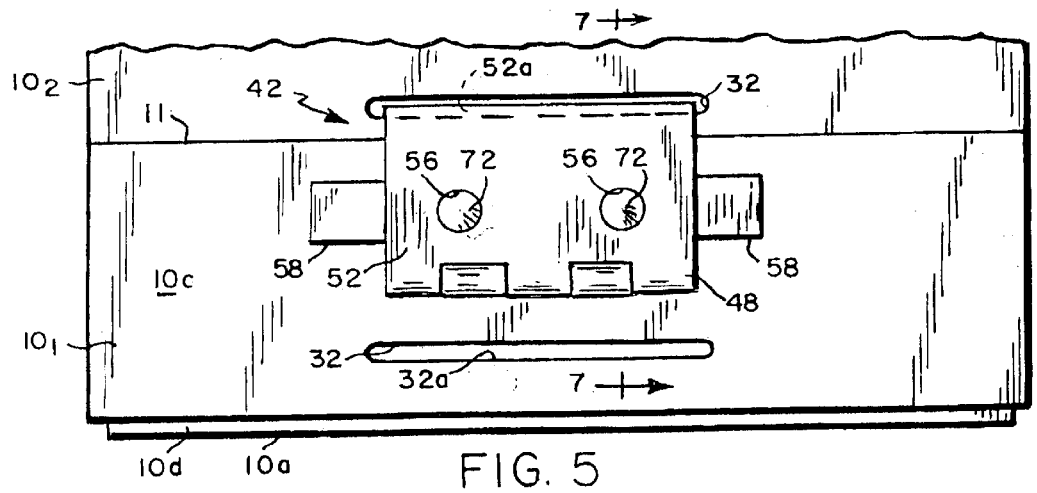
FIG. 5 is an end view of a tray for the FIG. 1 system illustrating a second latch embodiment, the latch being shown in its latching position.
Figure 6:
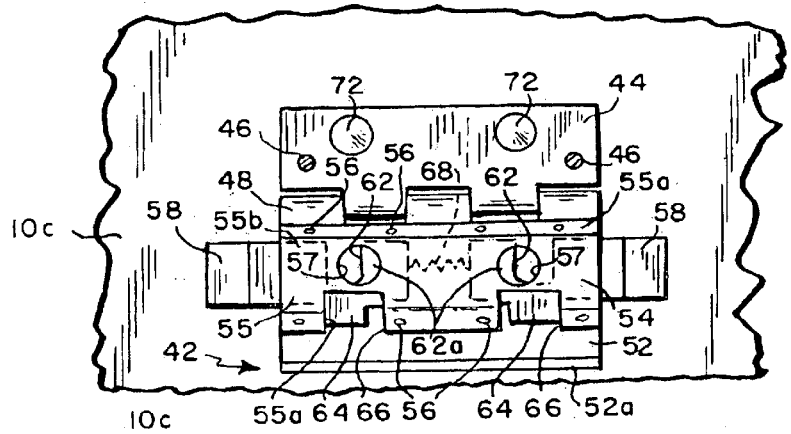
FIG. 6 is a view similar to FIG. 5 showing the latch in an unlatched fully open position.
Figure 7:
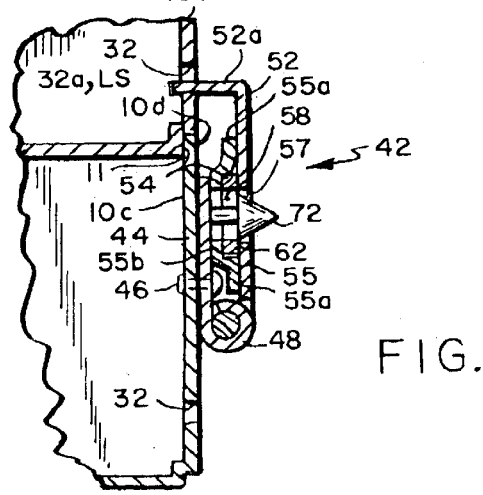
FIG. 7 is a sectional view taken along line 7—7 of FIG. 5.

Refer now to FIGS. 5 to 7 which illustrate another latch embodiment 42 which may be used on the trays depicted in FIGS. 1 to 3. As shown there, latch 42 comprises a generally rectangular base 44 which may be secured by fasteners 46 to the perimeter wall of the tray. Swingably connected by a hinge 48 to base 44 is an arm 52 whose upper edge margin is bent at a right angle to form a projection or flange 52a. Arm 52 functions in the same way as the arm 26 of flange 16 described above. In fact, the only appreciable difference between latches 16 and 42 is the mechanism for releasably locking the latch arm in its latching position as will be described presently.

As best seen in FIGS. 5 and 6, the latch arm 52 has a horizontal slide 54 open at both ends. The slide is formed by a plate 55 having upper and lower edge margins 55a,55a and a raised mid-portion 55b between those margins. Fastening means 56, i.e., slot welds, adhesive rivets, etc. at the edge margins 55a anchor the plate to the arm 52. The latch arm 52 and the plate 55 defining slide 54 are provided with aligned pairs of through holes 57,57. Also, slidably received in the opposite ends of slide 54 between arm 52 and plate 55 is a pair of mirror image sliders 58,58. Each slider 58 is formed with a hole or notch 62 and a tab 64 the latter projecting through an opening or slot 66 in the lower side of slide 54, i.e. in the plate 55. The sliders 58 are movable toward and away from each other between a locking position and an unlocking position. When the tabs are in their close-together unlocking position, the holes or notches 62 in the sliders are aligned with the pair of through holes 57,57 in the slider and latch arm and when the slides are in their locking position, the adjacent edges 62a of the slider holes 62 partially occlude the pairs of through holes 57,57 in the plate 55 and latch arm 52. The locking and unlocking positions of the sliders 58 are established by the engagement of the slider tabs 64 with the edges of the plate openings 66. Also, the sliders are biased away from each other toward their locking position by a spring 68 compressed between the opposing ends of the two sliders within slide 54 as shown in FIG. 6.

When the arm 52 of latch 42 is swung to its latching position shown in FIGS. 5 and 7, the pairs of openings 57 in the plate and latch arm are arranged to receive a pair of pointed barbed detents 72 projecting out from the latch base 44. In this, the detents 72 engage the occluding edges 62a of the slider holes 62 thereby wedging the sliders toward one another in opposition to the bias of spring 68 until those edges engage behind the detents 72 as shown in FIG. 7. At that point, the spring 68 urges the sliders 58 apart so that the edges 62a of holes or notches 62 engage behind the detents and lock the latch arm 52 in its latching position shown in FIGS. 5 and 7. The latch 42 may be unlocked to release the latch arm 52 by squeezing the sliders 58 together thereby aligning the slider holes 62 with the plate and latch arm holes 57, allowing the latch arm 52 to be swung away from the tray wall 10c. The locking could also be accompanied by a single slider biased laterally into engagement behind the barbs.

Figure 8:
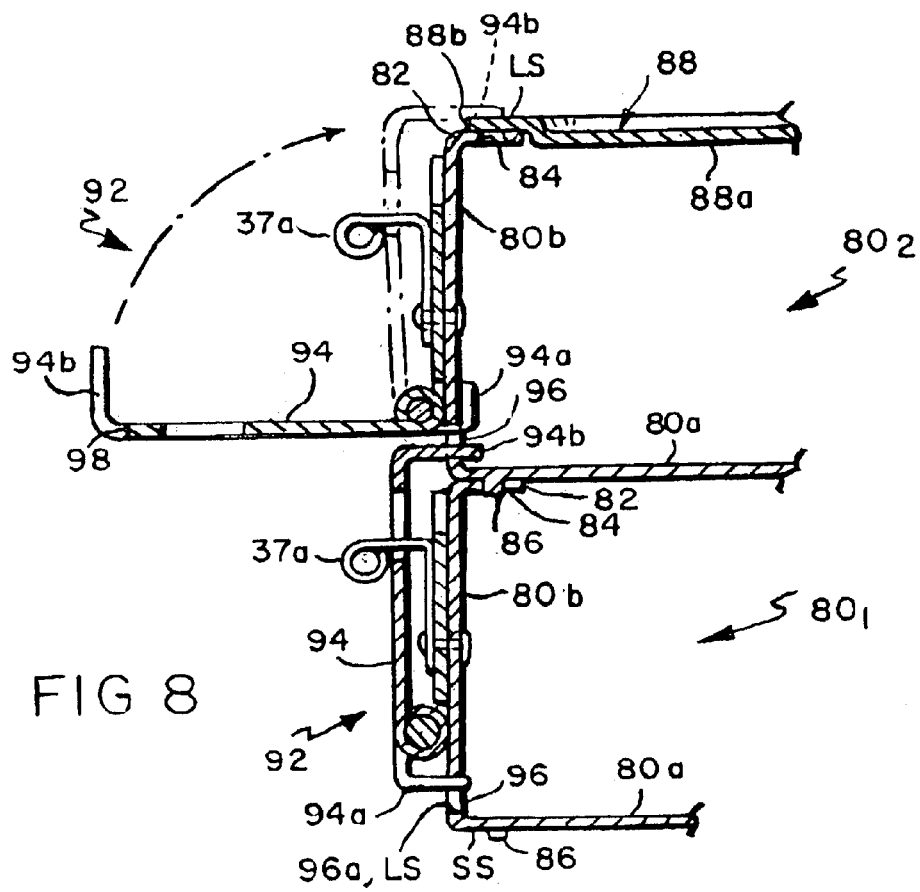
FIG. 8 is a view like FIG. 3 showing another tray system embodiment.

Refer now to FIG. 8 which illustrates another tray system embodiment composed of trays $80_1$, $80_2$, etc. In this case, the trays are fabricated of a metal, e.g. aluminum, stainless steel or the like. Each tray has a bottom wall 80a and opposite end walls 80b, 80b, but no side walls. Unlike the trays illustrated in FIG. 1, the end walls 80b of the trays illustrated in FIG. 8 are provided with an inwardly extending generally horizontal flange or lip 82 each lip or flange having one or more vertical holes or slots 84. Each of these holes or slots 84 is arranged to receive a pin or tab 86 extending down from the bottom wall 80a of an overlying tray in the stack so that all of the trays are maintained in vertical alignment. The pins or tabs 86 at the bottom of each tray may be struck from the bottom wall 80a of each tray or consist of separate pieces which are attached to the underside of the bottom wall by suitable fastening means.

The tray system in FIG. 8 may be topped off by a cover member shown generally at 88 which is shaped to nest between the end walls 80b of the uppermost tray in the stack. For this, the cover member 88 has a bottom wall 88a which fits between the end wall flanges 82 of the uppermost tray. The cover member 88 is formed with raised flanges or lips 88b, 88b which are arranged to seat on the flanges 82 of the uppermost tray so as to cover that tray. In other words, the illustrated cover member 88 is dished so that it seats on and covers tray $80_2$.

Figure 9:
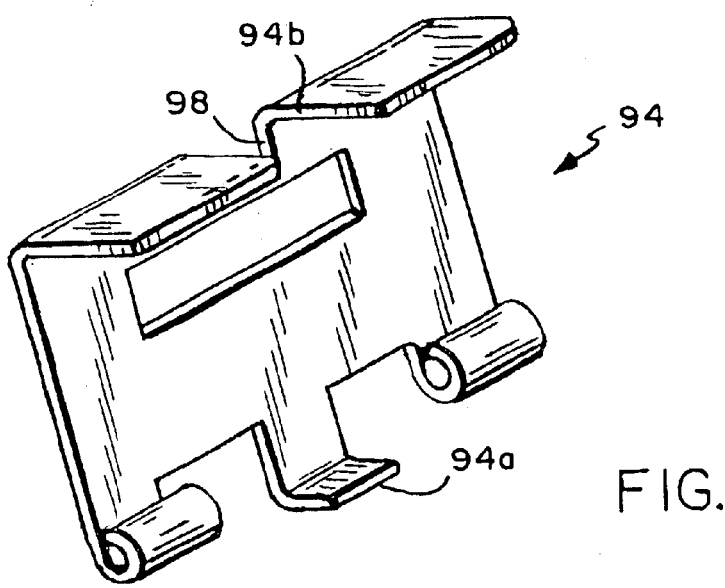
FIG. 9 is a perspective view of a portion of the FIG. 5 latch.

Each tray $80_1$, $80_2$, etc. includes latches 92 mounted to its end walls 80b,80b. Latches 92 are similar to those depicted in FIGS. 1 to 3. However, they can also be of the type illustrated in FIGS. 5 to 7. In any event, as best seen in FIGS. 8 and 9, each latch 92 includes an arm 94 which is somewhat different from the arms of the latches described above in that it has a tab 94a which extends it right angle from the inner or lower end of the arm. The tab 94a is arranged to project through a hole 96 in the endwall 80b of the associated tray. The hole 96 performs a dual function in that it provides clearance for the tab 94a and its lower edge 96a may function as the locating surface LS for that tray. In other words, the hole 96 is similar to the hole 32 in the FIGS. 1 to 3 trays except that it is somewhat higher in order to accommodate the tab 94a when the lever arm 94 swings between its latching and unlatching positions as will be described presently.

As shown in FIG. 8, the latch arm 94 can be swung between an open or unlatching position shown in solid lines at the upper tray $80_2$ and a closed or latching position shown in phantom at tray $80_2$ and in solid lines at $80_1$. When the latch arm 94 is in its unlatching position, it extends out at right angles from the endwall 80b of the associated tray, that position being established by the engagement of the tab 94a against the inside surface of the end wall 80b of that tray.

When the latch arm 94 is swung to its latching position, tab 94a is partially retracted from the corresponding hole 96 while a projection or flange 94b at the free end of the latch arm engages the latching surface LS of the overlying tray or the cover member 88. In the case of the tray, the latching surface is the lower edge 96a of the hole 96 and in the case of the cover member 88, the latching surface is the upper surface of the cover member flange or lip 88b.

While the latch arms 26 and 52 of the latches are shown as having continuous flanges 26a and 52a, the flange 94b of each latch arm 94 is provided with a notch or cut-out 98 as best seen in FIG. 9. Thus, when a latch arm 94 is in its latching position as shown on the lower tray $80_1$ in FIG. 8, the notch or cutout 98 in that latch arm will provide clearance for the tab 94a of the latch arm 94 on the overlying tray $80_2$ allowing the latter latch arm to be swung between its latching and unlatching positions as shown in phantom and solid lines, respectively. The FIG. 9 latch arm configuration is particularly suitable when the latches 92 are affixed to short or shallow trays.

It is apparent from the foregoing that the trays described above with their specially designed and positioned latches allow a plurality of trays having different heights to be nested together in a stack and covered to provide a fully enclosed package for storing and transporting surgical instruments and other articles.

It will thus be seen that the objects set forth above among those made from the preceding description are efficiently attained. Also, certain changes may be made in the above constructions without departing from the scope of the invention. For example, instead of the latches on each tray latching to an overlying tray, the latches may be inverted and mounted lower down on the tray perimeter walls so that they latch to latching surfaces formed on an underlying tray. Similarly, the latches could be mounted to the cover for securement to a latching surface of an underlying tray. Also, while the latching surfaces of the tray system are shown as being formed by slots or openings in the end walls of the tray, those edges could be formed by recesses, ledges or slots elsewhere on the perimeter walls of the trays, and by similar recesses, ledges or slots in the cover. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A tray system comprising a plurality of trays including at least one underlying tray and at least one overlying tray, said trays having substantially the same cross-sectional dimensions and the same or different heights, each tray having
    a bottom wall;
    a plurality of wall segments extending up from the bottom wall, each wall segment having an upper end;
    one or more seating surfaces at or adjacent to the bottom wall of the tray, said seating surfaces defining a seating surface plane;
    a plurality of latching surfaces, said latching surfaces defining a latching surface plane spaced a selected distance above the seating surface plane, and
    a plurality of latches, each latch having
        an arm with one end swingably mounted to one of the plurality of wall segments above one of the plurality of latching surfaces, and
        a projection on said arm spaced from said one end, said arm being swingable between a latching position wherein the associated projection is spaced above the upper end of the corresponding wall segment a distance substantially equal to said selected distance so that when the trays are arranged in any order in a stack, the seating surface(s) of the overlying tray(s) rest on the wall segment upper ends of the underlying tray(s) and the arms of the latches on the underlying tray(s) may be swung to their latching positions, whereby the projections on those arms engage the latching surfaces of the overlying tray(s) thereby securing together all of the trays in the stack to form a single compact transportable package.

2. The tray system defined in claim 1 wherein each tray has a perimeter wall extending up from said bottom wall and includes said wall segments.

3. The tray system defined in claim 1 wherein said adjacent trays have interfitting portions which maintain the plurality of trays in vertical alignment in the stack.

4. The tray system defined in claim 3 wherein the interfitting portions comprise
    downward projections adjacent to the seating surfaces of each overlying tray in the stack, and
    the upper ends of the wall segments of each underlying tray in the stack.

5. The tray system defined in claim 3 wherein the interfitting portions comprise
    depending keys extending from the bottom wall of each tray in the stack, and
    vertical keyholes at the upper ends of the wall segments of each tray in the stack and which are positioned to receive the keys of the overlying tray in the stack.

6. The tray system defined in claim 1 and further including a cover, said cover member including
    a top wall;
    means for positioning said cover relative to the wall segments of an uppermost tray in the stack, so that the cover covers said uppermost tray, and
    a plurality of coplanar cover latching surfaces formed in said cover at locations spaced around the top wall thereof so that when the cover is seated on the wall segments of the uppermost tray in the stack, the cover latching surfaces are located directly above the latches on said uppermost tray whereby when the arms of those latches are swung to their latching positions, the projections on those arms engage the cover latching surfaces thereby securing the cover to the uppermost tray in the stack.

7. The tray system defined in claim 6 wherein said cover also includes a plurality of handles mounted to the cover to facilitate carrying said package.

8. The tray system defined in claim 1 wherein each latch includes a stop for stopping the swinging motion of the latch arm away from the corresponding wall segment to establish the unlatching position of the latch arm.

9. The tray system defined in claim 1 wherein each latch also includes a lock for releasably locking the arm of each latch in its latching position.

10. The system defined in claim 9 wherein said lock includes
    a window in said arm, said window having an edge, and
    a flexible resilient keeper mounted to said base, said keeper having a portion which projects through said window and engages said edge when the arm is in its latching position.

11. The system defined in claim 9 wherein said lock includes
   one or more barbs extending out from the perimeter wall at said latch;
   one or more openings in said arm which receive said one or more barbs when said arm is in said latching position, and
   one or more sliders mounted to said arm and being adapted to interfit with said one or more barbs when the arm is in said latching position.

12. A sterilizer tray for a tray system comprising
   a bottom wall;
   a plurality of wall segments extending up from the bottom wall said wall segments having upper ends which define a rim plane;
   one or more seating surfaces at or adjacent to the bottom wall of the tray, said seating surface(s) defining a seating surface plane spaced parallel to the rim plane;
   a plurality of latching surfaces formed in said wall segments, said latching surfaces defining a latching surface plane spaced at a selected distance from seating surface plane, and
   a plurality of latches, each latch including
      an arm having one end swingably mounted to one of the plurality of wall segments above one of the plurality of latching surfaces, and
      a projection on said arm spaced from said one end, said arm being swingable between a latching position wherein the projection on that arm is spaced above the rim plane a distance that substantially corresponds to said selected distance and an unlatching position wherein the projection on that arm is spaced below said rim plane.

13. The tray defined in claim 12 wherein each latch also includes a lock for releasably locking the arm of each latch in its latching position.

14. The tray defined in claim 13 wherein said lock includes
   a window in said arm, said window having an edge, and
   a flexible resilient keeper mounted to said bases said keeper having a portion which projects through said window and engages said edge when the arm is in its latching position.

15. The tray defined in claim 13 wherein said lock includes
   one or more barbs extending out from the perimeter wall at said latch;
   one or more openings in said arm which receive said one or more barbs when said arm is in said latching position, and
   one or more sliders mounted to said arm and being adapted to interfit with said one or more barbs when the arm is in said latching position.

16. The tray defined in claim 15 wherein the lock also includes a spring for biasing said one or more sliders into locking engagement with said one or more barbs.

17. The tray defined in claim 12 and further including first tray portions at the upper ends of the wall segments and second tray portions at the bottom wall which may interfit with matching portions at similar overlying and underlying trays to maintain all of the trays in vertical alignment in a stack.

* * * * *